(12) United States Patent
Montgomery et al.

(10) Patent No.: US 6,281,265 B1
(45) Date of Patent: Aug. 28, 2001

(54) CURABLE COMPOSITIONS WITH ANTIMICROBIAL PROPERTIES

(75) Inventors: R. Eric Montgomery, Monterey, MA (US); Salim A. Nathoo, 577 S. Randolphville Rd., Piscataway, NJ (US) 08854

(73) Assignee: Salim A. Nathoo, Piscataway, NJ (US)

( * ) Notice: Subject to any disclaimer, the term of this patent is extended or adjusted under 35 U.S.C. 154(b) by 0 days.

(21) Appl. No.: 09/255,450

(22) Filed: Feb. 19, 1999

Related U.S. Application Data (60) Provisional application No. 60/075,176, filed on Feb. 19, 1998, provisional application No. 60/075,246, filed on Feb. 19, 1998, and provisional application No. 60/094,823, filed on Jul. 31, 1998.

(51) Int. Cl.⁷ .......................... A61K 7/043; A01N 25/34
(52) U.S. Cl. .......................... 523/122; 424/61; 424/409; 424/401; 424/405; 523/105; 523/113; 523/115
(58) Field of Search .......................... 523/105, 113, 523/122; 524/341, 348, 558, 560; 424/409, 61, 401, 405; 623/15

(56) References Cited

U.S. PATENT DOCUMENTS

| | | |
|---|---|---|
| 4,514,527 | 4/1985 | Bowen .......................... 523/115 |
| 4,659,751 | 4/1987 | Bowen .......................... 523/116 |
| 4,669,491 * | 6/1987 | Weisberg et al. . |
| 4,894,220 | 1/1990 | Nabi et al. .......................... 424/52 |
| 4,966,934 | 10/1990 | Huang et al. .......................... 524/315 |
| 4,978,391 | 12/1990 | Jones .......................... 106/35 |
| 5,098,696 | 3/1992 | Montgomery .......................... 424/61 |
| 5,270,351 | 12/1993 | Bowen .......................... 523/116 |
| 5,276,068 | 1/1994 | Waknine .......................... 522/28 |
| 5,338,773 | 8/1994 | Lu et al. .......................... 523/116 |
| 5,340,850 | 8/1994 | Shimasue .......................... 523/115 |
| 5,344,641 | 9/1994 | Gaffar et al. .......................... 424/49 |
| 5,385,728 | 1/1995 | Suh .......................... 424/54 |
| 5,424,058 | 6/1995 | Rajaiah .......................... 424/49 |
| 5,665,333 | 9/1997 | Homola et al. .......................... 424/54 |
| 5,676,745 | 10/1997 | Kelly et al. .......................... 106/35 |
| 5,686,064 | 11/1997 | Gaffar et al. .......................... 424/57 |
| 5,733,949 | 3/1998 | Imazato et al. .......................... 523/109 |
| 5,738,843 | 4/1998 | Montgomery .......................... 424/61 |
| 5,800,803 | 9/1998 | Mirajkar .......................... 424/54 |
| 6,022,549 * | 2/2000 | Dyer . |

FOREIGN PATENT DOCUMENTS

| | | |
|---|---|---|
| 223245 | 5/1987 | (EP) . |
| 381446 | 8/1990 | (EP) . |
| 705590 | 4/1996 | (EP) . |
| 3-118309 | 9/1989 | (JP) . |
| 03118309 | 5/1991 | (JP) . |
| 11049625 | 8/1997 | (JP) . |
| WO 89/10113 | 11/1989 | (WO) . |
| WO 89/10736 | 11/1989 | (WO) . |
| WO 98/48766 | 11/1998 | (WO) . |

OTHER PUBLICATIONS

McCourtie, et al., Journal of Medical Microbiology, 21:209–213 (1986).
Addy, Journal of Oral Rehabilitation, 8:131–142 (1981).
Budtz–Jorgensen, et al., Scandinavian Journal of Dental Research, 91(2):134–142 (1983).
Imazato, et al., J. Dental Res. 73(8):1437–1443 (1994).
Addy, et al., Journal of Oral Rehabilitation, 8:155–163 (1981).
Addy, et al., J. Oral Rehab. 6:111–117 (1979).
Imazato, et al., J. Osaka Univ. Dent. Sch. 35:5–11 (1995).
Chapters 11, 12 and 13 in Phillip's Science of Dental Materials, K.J. Anasavice, ed. 10$^{th}$ Ed., 1996 (pp. 237–313).
Barry, et al., "Susceptibility Tests: Diffusion Test Procedures," in Manual of Clinical Microbiology, 5$^{th}$ Ed. (Hausler, et al., eds.), Am. Soc. Microbiology (Washington), 1991.
"Green Monsters" in *Nails* (Nov. 1997).
Ehara, et al., J. Dent. Res. 79(3):824–828 (2000).

* cited by examiner

*Primary Examiner*—Peter Szekely
(74) *Attorney, Agent, or Firm*—Lerner, David, Littenberg, Krumholz & Mentlik, LLP (57) ABSTRACT

Novel curable compositions are disclosed which include a water insoluble antimicrobial agent. The curable compositions are useful in inhibiting the growth of bacteria on the surface of the curable composition, within the curable compositions and in a volume adjacent to the curable composition.

6 Claims, 1 Drawing Sheet

FIG. 1

FIG. 2

CURABLE COMPOSITIONS WITH ANTIMICROBIAL PROPERTIES

This application claims the benefit of U.S. Provisional Application No. 60/075,176 filed Feb.19, 1998, U.S. Provisional Application No. 60/075,246 filed Feb.19, 1998 and U.S. Provisional Application No. 60/094,823 filed Jul. 31, 1998 and hereby incorporates the subject matter of those applications by reference in their entireties for all purposes.

BACKGROUND OF THE INVENTION

1. Field of the Invention

This invention relates to improvements in curable compositions intended for use or placement in direct contact with a biological surface. More specifically, this invention discloses curable compositions with antimicrobial properties, together with methods for their use, which are useful for preventing microbial growth on one or more surfaces of the curable composition or within the curable composition or adjacent to the curable composition after curing and subsequent placement in contact with a biological surface.

2. Description of Related Art

Materials science has provided us with a plethora of compositions that can be transformed from an initial, malleable state to a final, non-malleable state, generally through the process of heating, the application of pressure, and/or the inducement of polymerization. Such compositions provide us with an array of materials that may be first molded into a desired shape, then subsequently induced to transform into a final, non-deformable shape identical (or nearly so) to the original molded shape. Such processes may employ heat or pressure (or both) to transform materials into a desired shape by manipulation of the physical properties of the material itself, or may alternatively utilize initiators and/or activators to begin a polymerization reaction throughout the shaped mass. Alternatively, a curing process may occur simply as a composition absorbs moisture from the surrounding environment. Such curing processes are seen in certain types of adhesives, such as urethanes-based caulks and denture adhesives.

The class of materials known as acrylics (which, for the purpose of this disclosure, shall mean compositions comprised wholly or in part of acrylate and/or methacrylate monomers and/or polymers, alone or in combination with each other and/or other unsaturated and/or saturated compounds) has gained acceptance as being particularly suited for the formation of prosthetics to be placed into contact with the body. In particular, acrylics have been used to form dental restorative materials, dentures, temporary crown and bridge materials, and artificial fingernails and toenails, as well as having been employed as adhesion promoters at the interface between a biological surface (herein defined as any external or internal surface of a living organism) and a prosthetic (in order to provide the extended wear time required of, for instance, a permanent dental restorative material). Curable acrylic compositions, when properly initiated or catalyzed, undergo free-radical addition reaction polymerization, which is exothermic (i.e. generates heats) in character.

As biological surfaces are invariably populated by a wide variety of microorganisms, inert objects (such as prosthetics or adhesives), when placed in contact with such surfaces are subject to surface colonization and, often, subsequent penetration by those same microorganisms. In addition, fluid infiltration at the interface between the biological and non-biological surfaces presents ideal conditions for the growth of microorganisms. In the absence of any protective mechanism to prevent such colonization, objects in contact with biological surfaces often become populated with a higher density of microorganisms than the original biological surface itself. Thus a prosthetic can become a breeding ground for potentially harmful microorganisms and subsequently itself become a source of infection to adjacent living tissue. For example, the occluded interface or margin between an inert object and a biological surface, due to the accumulation of moisture there (and often, the exclusion of oxygen, which results in an environment conducive to the growth of anaerobic microorganisms), can foster the development of microbial colonies in higher numbers than the same biological surface would have in a non-occluded state.

One example of this interfacial phenomenon is recurrent caries, which is though to be caused by the infiltration of microorganisms, in particular, those responsible for dental caries (tooth decay), into the interface margin between a dental restorative material (such as an amalgam or resin-based composite) and the natural tooth surface. In the process of preparing, placing and finishing a dental restoration, the marginal adaptation of the restorative material, in addition to the quality and strength of the bond between the restoration and the natural tooth surface, is of paramount importance to the restoration's longevity as a permanent prosthetic. If the adhesion of the restorative material is inadequate, or the shape of the restorative material is slightly non-conforming, oral fluids such as saliva, which constantly bathe the restoration, are able to infiltrate into the interface between the restorative material and the natural tooth. Microorganisms are carried along with the infiltrating fluids and may colonize the marginal space. The metabolites of certain microorganisms, such as *Streptococcus mutans* species, are potentially harmful to the natural tooth structure, and erosion of the tooth at the interface (recurrent caries and possible restoration failure) may occur over time.

Recurrent caries have been shown to be a major cause in the failure of dental restorations. The failure is thought to occur due to penetration of pathogenic organisms which as *S. mutans* into the tooth structure along the cavity wall through microleakage and/or accumulation of bacteria at the margins, or interface, between the restorative material and the tooth. The incidence of recurrent caries around restorations involving enamel can be reduced by using fluoride containing restorative materials. However, the amount of fluoride released has been shown to decrease significantly with time and thus cariostatic ability of these restorative materials over a long term remains unclear. To overcome this advantge, attempts have been made to supplement restorative materials with antimicrobial agents. Addition of chlorhexidine, a water soluble catonic antimicrobial agent to composite restorative materials ahve largely been unsuccesful because of the loss of efficacy and deterioration of physical properties. Attempts have also been made to add other types of antimicrobial agents to restorative materials. Recently, Imazato, et al. U.S. Pat. No. 5,733,949 incorporated methacryloyloxydodecylpyridinium bromide (MDPB) to experimental composites and showed that the attachment of *S. mutans* to surfaces of the restorative material was reduced. However, unlike chlorhexidine, no zone of inhibition was evident by the disk diffusion method, indicating that the agent is not released oris released at sub MIC levels. This finding suggests that MDPD has a potential disadvantage becasue it does not solve the problem of permeation of bacteria through the enamel-restoration interfaces and destroying bacteria in the cavity preparation.

The incidence of recurrent caries around restorations involving enamel can be reduced by using fluoride containing restorative materials. The purpose of the fluoride is to convert hydroxyapatite to fluorapatite, which is more resistance to acid attack. The major disadvantage with the use of fluoride is that it does not have significant antimicrobial activity and is easily washed away or diffuses away due to its high degree of solubility in the surrounding aqueous medium of the oral cavity.

To overcome one of the disadvantages indicated above, attempts have been made to add antimicrobial agents that are more effective against oral microorganisms than fluoride to dental materials, such as denture acrylics and denture soft liners. Chlorhexidine and its acetate or gluconate salts are water-soluble cationic antimicrobial agents capable of inhibiting or killing a wide variety of oral pathogens. However, incorporation of chlorhexidine salts in such compositions resulted in the rapid release of the highly water-soluble antimicrobial agent and subsequent impairment of the cured material's physical properties. See, for example, J. McCourtie, et al, Effect of Saliva and Serum on the Adherence of Candida Species to Chlorhexidine-treated Denture Acrylic in Journal of Medical Microbiology, Vol. 21, (1986), 209–213, in addition to M. Addy, In Vitro Studies into the Use of Denture Base and Soft Liner Materials as Carriers for Drugs in the Mouth in Journal of Oral Rehabilitation, Vol. 8, (1981), 131–142.

Attempts have also been made to add other types of antimicrobial agents to restorative materials. Recently, Imazato, et al. U.S. Pat. No. 5,733,949 incorporated methacryloyloxydodecylpyridinium bromide (MDPB) to experimental composites and showed that the attachment of S. mutans to surfaces of the restorative material was reduced. However, unlike chlorhexidine, no zone of inhibition was evident by the disc diffusion method, indicating that the agent is not released or is released at sub minimum inhibitory concentration (MIC) levels. This finding suggests that MDPB has a potential disadvantage because it does not solve the problem of permeation of bacteria through the enamel-restoration interfaces and destroying bacteria in the cavity preparation.

It has been shown that demineralization of surface enamel is caused by acid production from S. mutans and other cariogenic organisms, while demineralization along the cavity wall is caused by a combination of acid attack on outer enamel surfaces and additional acid attack through the gaps or microleakage between the cavity wall and the restoration. Both types of acid attack can be prevented by cariostatic agents deposited on the outer surfaces, at the cavity walls and in the areas of microleakage. Hence, the presence of cariostatic agents or antimicrobial agents may reduce or eliminate caries formation via reducing the solubility of enamel or inhibition of bacterial activity.

Attempts have also been made to add water-insoluble antimicrobial agents to dental materials for the purpose of inhibiting surface growth. See J. Osaka Univ. Dent. Sch., vol. 35, pp. 5–11, 1995. In JP Patent Application No. 3-118309, triclosan was added to the monomer of a light-curable composite material and the material subsequently cured with a curing light. The release of the triclosan into the surrounding medium was extremely low (0.02 micrograms/ml) for most of the compositions tested. As a result, the investigators did not observe the reduction of bacteria around disks made from the various triclosan-impregnated compositions until the triclosan concentration was well in excess of 1 percent by weight, namely 4% by weight. Only at 4 percent by weight triclosan, was there a slight (<1 mm) zone of bacterial inhibition around the disk prepared from a light-cured composite restorative material. The cured composition was ineffective at levels below 4% triclosan in inhibiting or destroying bacteria in the medium surrounding (i.e., not in direct contact with) the restoration.

Dental restorative materials, especially resin-based composites (which are generally composed of a fluid matrix carrier based on modified acrylic monomers and/or polymers, together with a dispersed inorganic phase composed of glass, silica, and other finely divided materials), are able to support the growth of microorganisms on surfaces exposed to the oral environment. Such surfaces are seen to accumulate plaque and tartar to a degree often greater than an exposed natural tooth surface. Again, such accumulation may have an impact on the health of adjacent natural hard and soft tissue surfaces, for instance, the irritation of gingival tissues adjacent to a heavily colonized restorative surface.

Another example of this interfacial phenomenon occurs in the artificial fingernail art. Artificial fingernails are often formed by dipping an artist's brush into a liquid acrylic monomer, which contains a polymerization initiator (typically a tertiary amine such as dimethyl-p-toluidine). The wetted brush is then contacted with a reservoir containing an acrylic polymer, which also contains a polymerization initiator (such as benzoyl peroxide). The resulting slurry of liquid and powder that adheres to the brush is transferred to the natural fingernail surface and the polymerization initiators interact to cause polymerization of the slurry into a hard mass within a period of about three to seven minutes.

Although the natural fingernail surface is typically prepared in such a fashion as to attempt to assure the exclusion of microorganisms prior to placement of the artificial fingernail slurry, oftentimes the preparative procedure results in a natural nail surface that is less than sterile. Even if sterile conditions on the natural fingernail surface were achievable in practice (which they are not), an insufficient bond strength between the polymerized artificial fingernail and the natural nail surface will result in the potential for fluid infiltration into the interfacial space created by a partial separation. Such fluid infiltration can result, as in the dental restorative example above, in the colonization of the natural fingernail/artificial fingernail interface by externally-derived microorganisms (such as Pseudomonas aeruginosa, which has been identified as the most common source of nail infections).

Another example of the problems associated with surface colonization of acrylic prosthetics is found in dentures. The extended wear time achieved by more modern denture adhesive formulations has resulted in a longer residence time for dentures, which are based on acrylic polymers. The preparation of a denture is a process well known in the art and is more fully described in references such as Phillip's Science of Dental Materials, K. J. Anusavice, ed. 10$^{th}$ Edition, 1996 (W. B. Saunders & Co). A typical denture is prepared by taking an impression of a patient's edentulous arch, creating a dental cast from the impression, and then creating a resin record base on the casting. Subsequently, wax is added to the record base and the artificial teeth are positioned in the wax. A pressure container, called a "flask" is chosen and the completed tooth arrangement is encased in an investment medium. The flask is then opened and the wax eliminated. The denture base material is then introduced into the mold cavity and the complete assembly polymerized by either a combination of heat and pressure, or alternatively through a chemical curing process. The flask is opened and the finished denture removed.

Extended denture retention time has resulted in a longer period during which oral microorganisms can utilize the denture adhesive composition and then enter the surface of the denture itself as a growth medium. Growth of oral microorganisms within denture adhesive compositions and on the surfaces of dentures have been identified as causes of oral malodor associated with denture use. Microorganism growth on the denture can be promulgated by the adjacent growth in the denture adhesive. Denture-induced stomatitis (DIS) and inflammatory papillary hyperplasia (IPH) are conditions that are known to result from dentures with microorganism-contaminated surfaces (see, for example, E. Budtz-Jorgensen, et al, in Quantitative Relationship between Yeast and Bacteria in Denture-Induced Stomatitis, Scandinavian Journal of Dental Research, Vol 91(2) (1983), 134–142).

In order to provide additional comfort to wearers of dentures, soft relining materials are often employed to facilitate better adaptation of the attachment surface (generally in the region of the palate) and to provide a "cushion" between the hard denture surface and the point of attachment in the oral cavity. Soft reliners are typically self-curing (autopolymerizing) acrylic materials that utilize acrylic monomers and/or polymers with a relatively low glass transition temperature ($T_g$). Alternatively, plasticizers such as dibutyl phthalate are used to provide elasticity to the cured soft reliner composition. The high flexibility and softness of such materials results in a greater degree of porosity, thus increasing the likelihood of microbial colonization. In particular, it has been shown that soft reliner materials support the growth of Candida albicans, a fungal organism thought to be associated with denture stomatitis. Previous attempts to limit the growth of microorganisms in soft reliner materials have been made through the inclusion of water-soluble antimicrobial agents such as zinc undecylenate and undecylenic acid.

The durability of the antimicrobial effect in prior art compositions containing one or more water-soluble antimicrobial agents is relatively poor, presumably due to the rapid rate at which the agent is released from the material into the surrounding aqueous medium. More often than not, the presence of a water-soluble molecule within a cured composition will contribute to the deterioration of said composition's physical properties; it is presumed that the voids left in a cured composition's polymeric structure by the solubilized antimicrobial can render the material unsuitable or its intended purpose.

There is thus a need for improved compositions and methods that address the problems associated with acrylic prosthetics and adhesives placed in contact with a biological surface.

In particular, there is a need for improved compositions and methods for their use that prevent the growth of microorganisms at the interface between a biological surface and a non-biological surface.

Furthermore, there is a need for improved curable compositions and methods for their use that can inhibit or kill microorganisms in the surrounding medium in which they are placed.

BRIEF SUMMARY OF THE INVENTION

The present invention discloses curable compositions with antimicrobial properties, together with methods for their use as or in conjunction with prosthetics placed in contact with a biological surface. Said biological surface is a potential source of microbial contamination, and the inventive compositions and methods are useful in substantially inhibiting surface colonization by microorganisms, as well as colonization within the curable composition itself. Prosthetic materials formed from the inventive compositions including a water insoluble antimicrobial agent and placed in contact with a potential source of microorganisms in an aqueous environment have unexpectedly been shown to substantially prevent the growth of microorganisms adjacent thereto. In addition, the prosthetic materials formed from the inventive compositions have further been shown to advantageously substantially prevent the growth of microorganisms within a volume surrounding the prosthetic material. That volume is referred to herein as a "zone of inhibition" and is defined as the volume immediately adjacent to the prosthetic material and extending a distance away from the prosthetic material sufficient to inhibit the growth of microorganisms within the zone. The zone of inhibition is determined in part by the degree of crosslinking of the curable composition, the concentration of the water insoluble antimicrobial agent within the cured composition, and the release of the water insoluble antimicrobial agent from the cured composition when placed in an aqueous environment. The zone or volume of inhibition is characterized by a concentration gradient of the water insoluble antimicrobial agent extending away from the cured composition. This aspect of the present invention is particularly advantageous as the cured compositions of the prosthetic materials or adhesives not only prevent surface colonization of microorganisms thereon, but also prevents colonization of microorganisms at locations a distance away from the prosthetic material, such as adjoining or contacting biological or prosthetic material or spaces between the compositions of the present invention and adjacent biological or prosthetic material.

A wide variety of compositions, for example those formed from materials known as acrylics, are available which are intended for placement and use within the oral cavity for extended periods of time. For the purpose of this disclosure, the term acrylic shall be interpreted to mean any monomeric or prepolymeric compound or mixture of compounds having at least one unsaturated moiety capable of undergoing a polymerization reaction that produces a higher molecular weight compound. The polymeric materials resulting from the aforementioned polymerization reaction will also be termed an acrylic. Unsaturated moieties include acrylate, methacrylate, and/or vinyl groups. Many of these compositions form prostheses such as dentures and temporary restorative materials and must be shaped to conform to an individual's dentition or mouth to allow for comfortable wear after extended periods of time. In order to accomplish this goal, many of these compositions are provided in a curable form, so that after being shaped to an individual's needs, a chemical reaction can be initiated which will render the once malleable mass into a composition that resists a change in shape and size. According to the present invention, one or more water insoluble antimicrobial agents can be included within the ingredients forming the curable composition and then the ingredients can be cured to form the prosthesis or adhesive of the present invention. The antimicrobial agents remain inert to monomers or prepolymers which may be used to produce the cured composition. According to one embodiment, an antimicrobial agent is mixed together with one or more of the composition ingredients. Once all of the intended ingredients are mixed or otherwise combined together, the monomers or prepolymers are polymerized to produce a cured composition which incorporates the antimicrobial agent. The cured composition is crosslinked to an extent such that it allows the antimicrobial agent to inhibit the growth of bacteria within a volume or zone of inhibition surrounding the cured composition. In this manner, the cured composition includes an antimicrobial agent and further includes a zone or volume of inhibition surrounding the cured composition within which the growth of microorganisms is inhibited.

The compositions of the present invention are curable through a variety of polymerization reactions that may be initiated by, for example, heat, light, and/or chemical catalysts. The cured compositions when placed in an oral cavity are unique in their ability to allow the antimicrobial agent to inhibit microbial growth on and within the cured composition and within a volume or zone of inhibition of the cured composition after placement in the oral cavity, and according to one embodiment of the invention, at concentrations of the antimicrobial agent of less than 4% by weight of the curable composition.

In general, the class of antimicrobials broadly described as water-insoluble, non-cationic antibacterial agents have utility in the present inventive compositions and methods. More specifically, useful antimicrobial agents are selected from the group consisting of halogenated diphenyl ethers, halogenated salicylanilides, benzoic esters, halogenated carbanalides, and phenolic compounds. The most preferred antimicrobial agents are substantially water-insoluble members of either the halogenated diphenyl ether group or the phenolic group, in particular those compounds described in detail in U.S. Pat. Nos. 4,894,220 and 5,800,803, which are incorporated herein by reference. A preferred antimicrobial compound is triclosan. It is to be understood that the present invention is not intended to be limited to the specific antimicrobial agents described herein and in U.S. Pat. Nos. 4,894,220 and 5,800,803 incorporated by reference, but that one of skill in the art would readily identify useful antimicrobial agents based upon the disclosure herein.

In general, the concentration of the water-insoluble antimicrobial compound will be at least about 0.10 percent by weight of the ingredients of the curable composition as a whole, depending upon the solubility of the antimicrobial compound in the curable composition. However, any concentration of a substantially water-insoluble antimicrobial agent that provides for inhibition of microorganisms on the surface of, and at some finite distance from, a cured composition placed in contact with a biological surface is contemplated to be within the scope of the present invention. It is understood that different curable compositions will have an effect on the release rate of the antimicrobial agent, and as such, the curable composition carrier and the antimicrobial agent are interrelated with respect to the concentration of antimicrobial agent required.

Accordingly, it is an object of the present invention is to provide improved acrylic compositions and methods for their use that can limit or prevent the growth of microorganisms on one or more of its surfaces for an extended period of time.

It is a further object of this invention to provide improved curable acrylic compositions and methods for their use that can limit or prevent the growth of microorganisms at one or more of its surfaces when exposed to or in contact with a potentially infective biological surface.

It is yet another object of this invention to provide antimicrobial acrylic compositions that can be shaped and subsequently cured in situ on a biological surface.

It is yet another object of this invention to provide antimicrobial acrylic compositions that can be shaped and subsequently cured prior to being placed in contact with a biological surface.

It is still a further object of this invention to provide compositions and methods for their use for the purpose of preventing microbial contamination at the interface between a biological surface and a non-biological surface in contact therewith.

Other objects, features and advantages of certain embodiments of the present invention will become more fully apparent from the following description taken in conjunction with the accompanying claims and figures.

DETAILED DESCRIPTION OF CERTAIN PREFERRED EMBODIMENTS

The principles of the present invention may be applied with particular advantage to obtain curable compositions and methods useful in inhibiting the growth of microorganisms on or within a volume surrounding a prosthesis intended to be placed adjacent to or contacting biological tissue. Applications of the present invention include prostheses intended to be placed within an oral cavity, adhesives used to secure dental prostheses, as well as, cosmetic prostheses such as artificial fingernails and adhesives related thereto.

According to one embodiment of the present invention, the curable compositions of the present invention may be prepared according to methods well known in the art using commercially available curable compositions intended for use in oral cavities, such as Herculite XRV (Kerr Corporation, Orange, Calif.). Although any commercially available curable composition intended for placement in the oral cavity is contemplated to be within the scope of the invention, the antimicrobial curable compositions described herein are preferable of the class of (meth)acrylate monomers and polymers, containing free radical polymerization initiators appropriate to the desired mode of cure (heat, light, etc.). According to the present invention, the compositions cure in a manner to produce a matrix allowing activity of the antimicrobial agent outside of the cured composition itself. This can occur through release mechanisms such as elution, diffusion or other release mechanisms having first, second, or third order kinetic release rates. While not intending to be bound by any particular scientific theory, it is believed that the compositions are cured in manner to produce a crosslinked polymer system allowing for the continued and sustained release of the antimicrobial agent. Curable compositions used as denture materials, denture reline materials (both soft and hard), denture adhesives, permanent restorative materials, adhesion promoting agents, luting cements, and cavity liners are seen to unexpectedly benefit from the inclusion of water-insoluble antimicrobial compounds of the present invention in a manner to produce a volume or zone of inhibition within which the growth of bacteria is inhibited.

Commercially available curable compositions used as dental composite resins and artificial fingernail compositions generally consist of a polymerizable monomer such as an acrylate or prepolymer species, a powdered filler, and a polymerization initiator and or catalyst species. It is possible to formulate the inventive compositions in one part, or single component form, or alternatively compositions may be provided that include separate components, for instance, as a liquid and a powder, or alternatively as two pastes. The two components are intended to be mixed together shortly before the intended polymerization reaction is to take place. Additional components may also be included, such as crosslinking comonomers, polymerization initiators, polymerization accelerators, photoinitiators, UV light absorbers, pigments, dyes and the like. It is to be understood that embodiments of the present invention are not to be limited to any particular curable composition, but that one of skill in the art will identify suitable curable compositions based upon the disclosure herein.

Specific monomers useful in the above applications include, but are not limited to, methyl methacrylate, ethyl methacrylate, n-propyl methacrylate, isopropyl methacrylate, n-butyl methacrylate, isobutyl methacrylate, hydroxyethyl methacrylate, hydroxypropyl methacrylate, hydroxybutyl methacrylate, propylene glycol monomethacrylate, poly(ethylene glycol) monomethacrylate, isobornyl acrylate, isobornyl methacrylate, methoxyethoxyethyl methacrylate, ethoxyethoxyethyl methacrylate, tetrahydrofurfuryl methacrylate, acetoxyethyl methacrylate, and other monofunctional methacrylate and acrylate compounds and the like.

Prepolymers, which are herein defined as polymerizable compounds having one or more polymerizable groups, in addition to having a molecular weight in excess of about 300 daltons, are selected from the group including, but not limited to, 2,2-bis[4'-(3"-methacryloyl-2"-hydroxypropoxy)phenyl]propane(bis-GMA), ethoxylatedbisphenol A dimethacrylate, and urethane dimethacrylate (the reaction product of 1 mole of 2,2,4-trimethylhexamethylene diisocyanate with 2 moles of hydroxyethyl methacrylate) and the like.

Crosslinking comonomers include ethylene glycol dimethacrylate, diethylene glycol dimethacrylate, trimethylene glycol dimethacrylate, trimethyolpropane trimethacrylate, 1,4-butanediol dimethacrylate, 1,6-hexanediol dimethacrylate, 1,12-dodecanediol dimethacrylate, polyethylene glycol dimethacrylate, and the like.

Suitable fillers include powdered, granular, particulate, or otherwise finely divided inorganic materials, such as quartz, colloidal silica, alumina, hydroxyapatite, fluoroaluminosilicate glass, titanium dioxide, pyrogenic silica, precipitated silica and a variety of glasses and/or ceramics that optionally contain small amounts of heavy metals (barium, strontium, zirconium, etc), as well as powdered, granular, particulate, or otherwise finely divided organic materials including polymers such as poly(methyl methacrylate), poly(ethyl methacrylate), poly(butyl methacrylate), poly(ethyl-co-methyl methacrylate), poly(methyl vinyl ether-co-maleic anhydride), poly(acrylic acid), poly(methacrylic acid), poly(vinyl pyrollidone), poly(vinyl acetate), poly(vinyl butyryl), polyethylene, polypropylene, polytetrafluoroethylene, and the like. Inorganic fillers may be surface-modified, for instance with a methacrylate-functional silane compound, in order to improve the compatibility after polymerization of the inorganic filler with the surrounding organic fluid matrix.

Polymerization initiators may be advantageously employed in the inventive compositions at a concentration from about 0.1% to about 5.0% by weight and include peroxides, such as benzoyl and lauroyl peroxide, in addition to 5-butyl barbituric acid, 1-benzyl-5-phenyl barbituric acid, and other 5-alkyl or 5-aryl barbituric acid compounds and the like.

One or more polymerization accelerators that work in conjunction with the initiator to promote or improve the speed of polymerization may be advantageously included in the inventive compositions at a concentration of from about 0.1% to about 7.0% by weight. Accelerators such as N,N-dimethyl-p-toluidine, N,N-dihydroxyethyl-p-toluidine, ethyl-p-dimethylamino benzoate, dimethylaminoethyl methacrylate, N-(2-cyanoethyl)-N-methyl aniline, and other amino-functional compounds and the like are of particular utility in this respect.

In order to achieve a normal level of storage stability, especially for compositions that are cured through a free-radical curing mechanism, it may be desirable to include a conventional polymerization inhibitor. Examples of such inhibitors include hydroquinone monomethyl ether (MEHQ) and 2,6-di-tert-butyl-4-methylphenol (BHT or butylated hydroxytoluene) and the like. Some of the non-cationic water-insoluble antimicrobial agents described herein, for instance, the phenolic group-containing compounds, may have additional utility in this respect, i.e., as both an antimicrobial agent and as a polymerization inhibitor. Polymerization inhibitors may be included up to and including about 1.0% by weight of the composition.

The compositions may additionally contain one or more photoinitiators in order to render the composition's combined liquid and solid components sensitive to light, thereby effecting polymerization by actinic energy at a wavelength or wavelengths corresponding to the spectrum of said photoinitiators. Examples of useful photoinitiators include camphorquinone, benzil, 2-hydroxy-2-methyl-1-phenyl-propane-1-one (Darocure 1173, EM Chemicals, Hawthorne, N.Y.), and 1-hydroxycyclohexyl phenyl ketone (Irgacure 184, Ciba-Geigy Corporation, Hawthorne, N.Y.) and the like. The above photoinitiators may be included in the composition at a level of from about 0.1% by weight to about 6.0% by weight.

In order to prevent polymer degradation and yellowing from UV light after the polymerization process has been completed, a UV light absorber may be included in the composition at a level from about 0.1% by weight to about 3.0 percent by weight. Examples of suitable UV light absorbers found to have utility in the present inventive compositions are 2(2'-hydroxy-5'-methyl phenyl) benzotriazole (Tinuvin P, Ciba-Geigy Corporation, Hawthorne, N.Y.), 2-hydroxy-4-methoxybenzophenone and 2-cyano-3,3'-diphenylacrylic acid 2'-ethylhexyl ester (Uvinul M40 and Uvinul N539, respectively, BASF, Ludwigshafen, Germany) and the like.

The inventive compositions may also contain from about 0.5% to about 5.0% of a pigment or dye, in order to adjust the color of the resulting polymerized composition. For example, a red lake pigment and titanium dioxide are added to a denture base polymer composition in order to provide pigmentation that closely matches that of the oral mucosa. Suitable pigments and dyes include, but are not limited to, titanium dioxide, zinc oxide, insoluble lakes, and soluble dyes and the like. Pigments based on, for instance, barium may be added in order to make the resulting polymerized composition radiopaque to x-rays. Other radiopaquing fillers may also be advantageously included.

According to the present invention, a water-insoluble antimicrobial agent is included within the curable composition to not only inhibit the growth of both gram negative and gram positive bacteria on the surface of and within the cured composition in an aqueous environment, but also to inhibit the growth of both gram negative and gram positive bacteria within a volume surrounding the composition, termed herein as a "zone of inhibition". The zone of inhibition is used to define the area immediately adjacent and radially or perpendicularly outward (in the case of a round object) from an object in which the growth of a particular microorganism (or mixture of microorganisms) is inhibited. When an object possessing antimicrobial properties is placed on or within a growth medium that has been inoculated with a microorganism, it is observed that only in areas at a certain distance from the object will the organisms grow. This is due to a concentration gradient of antimicrobial compound that extends outward from the object, decreasing in amount moving further away from the object. The ability of antimicrobial compounds and objects containing such compounds to inhibit the growth of microorganisms at some distance from the surface of the releasing substrate can be determined using a disk diffusion assay., such as a Kirby-Bauer test. It is a convenient and relatively simple assay procedure for the antimicrobial-releasing capacities of the inventive curable compositions. The ability of the curable composition of the present invention to inhibit the growth of bacteria in an aqueous environment at locations away from the curable composition itself, is especially surprising given that the antimicrobial agent of the present invention is water insoluble, as compared to the use of water soluble or slightly water soluble antimicrobial agents.

Water-insoluble antimicrobial compounds useful in the present invention may be selected from the following group, which includes halogenated diphenyl ethers, halogenated salicylanilides, benzoic esters, halogenated carbanalides, and phenolic compounds. The most preferred antimicrobial agents are substantially water-insoluble members of either the halogenated diphenyl ether group or the phenolic group, in particular those compounds described in detail in U.S. Pat. Nos. 4,894,220 and 5,800,803, which are incorporated herein by reference.

The most preferred water-insoluble antimicrobial agent (herein defined as an antimicrobial compound having a solubility in distilled water at 25° C. of less than 1000 ppm) is triclosan (trade name Irgasan DP300). Triclosan (2,4,4'-trichloro-2'-hydroxydiphenyl ether, CAS No. 338034-5) is a broad spectrum antimicrobial with a molecular weight of 289.5, having very limited water solubility at physiological temperatures (20 ppm in distilled water at 20° C. and 40 ppm in distilled water at 50° C.). The safety of triclosan has been well established and its use in oral care products, primarily water-based toothpastes in which the triclosan, typically at a concentration of about 0.30 percent by weight, has been solubilized.

According to one embodiment of the present invention, the concentration of the water-insoluble antimicrobial compound will be at least about 0.10% percent by weight of the ingredients formulating the curable composition, depending upon the solubility of the antimicrobial compound in the ingredients. According to an alternate embodiment, the concentration of the antimicrobial agent is less than 4%, including 3%, 2%, and 1%. More preferably., the concentration of the water-insoluble antimicrobial compound will be in the range of between about 0.25 percent and about 5.0 percent and more preferably in the range of about 0.3 percent to about 1.0 percent. In the broadest sense, the concentration of an individual antimicrobial compound may vary from about 0.01 percent to about 10 percent by weight of the cured composition, in accordance with a particular composition's intended use or purpose. The composition's physical properties prior to curing (such as solvent content that, due to evaporation, will not ultimately be part of the composition after placement onto a biological substrate) and in a cured form (determined by the degree of crosslinking) can greatly affect the amount of antimicrobial compound required. In addition, the cured compositions include a volume or zone of inhibition surrounding the cured composition within which the growth of bacteria is inhibited. It is recognized and in some cases desirable that the curable composition may be manipulated in its ability to release the antimicrobial compound into the surrounding medium. Such manipulation can be accomplished by increasing or decreasing the amount of, for instance, crosslinking in the cured composition, so as to prevent the antimicrobial compound from being released out into the environment too quickly. As differences in the water solubility of antimicrobial compounds exist, some compounds may be advantageously included in compositions that, when cured, release said antimicrobial into the surrounding medium at various rates. In this fashion, the cured composition becomes a partial determinant of the rate of antimicrobial diffusion into the surrounding volume, similar to a controlled-release device (such as an encapsulant or transdermal patch).

In the broadest sense, the level of antimicrobial compound optimally included in a particular inventive composition is the minimum concentration which will, for an extended period of time, prevent the growth of microorganisms on the surface of and within a limited zone around the cured composition. An extended period of time is herein defined as the amount of time during which the cured composition is in contact with the biological surface and during which the cured composition is exposed to potential colonization by one or more microorganisms. Preferred extended times include from a few days, to a few weeks to few months and even years.

The following examples are set forth as being representative of the present invention. These examples are not to be construed as limiting the scope of the invention as these and other equivalent embodiments will be apparent to one of skill in the art in view of the present disclosure, tables, figures and accompanying claims.

EXAMPLE I

A commercially available permanent restorative material was modified to include a water-insoluble antimicrobial agent as follows:

TABLE 1

| Ingredient | Percent | | | | |
| --- | --- | --- | --- | --- | --- |
| | Control A | Control AK (Kneaded) | B | C | D |
| Herculite XRV | 100 | 100 | 99.75 | 99.5 | 99 |
| Triclosan | 0 | 0 | 0.25 | 0.5 | 1 |
| TOTAL | 100 | 100 | 100 | 100 | 100 |

In general, syringes of the Herculite XRV (Kerr Corporation, Orange, Calif.) were emptied into a tared plastic weighing cup (on a balance accurate to 0.001 grams) under low light conditions (this material is a light-activated permanent restorative material sensitive to light between the wavelengths of 400 and 500 nanometers). The syringes were saved for refilling after admixture with the triclosan. The correct amount of triclosan was calculated and weighed out on an analytical balance accurate to 0.0001 grams. The triclosan was combined with the restorative material under the same low light conditions as above, the blending procedure consisting of a thorough kneading, by hand, of the triclosan powder into the putty-like restorative material. A total of 5 minutes of kneading was done for each sample, after which the blended restorative material was carefully placed back in to the original syringe for storage. The control sample (A) was also kneaded (AK) in the same fashion as the samples containing triclosan, in order to maintain consistency in all testing. When required, compositions A, AK, B, C, and D were shaped into discs and then cured to produce representative examples of a dental prosthetic. The cured composition containing the antimicrobial agent was studied to determine whether the antimicrobial agent was released from the cured composition at levels greater than the MIC (minimum inhibitory concentration) for S. mutans at baseline and after two weeks of washing.

Specifically, composite restorative material (Kerr, Herculite XRV™) was obtained from Schein (Long Island, N.Y.). S. mutans (ATCC 25175) were purchased from American Type Culture Collection (Virginia). Brucella Broth (Difco) was obtained from VWR, NJ. Triclosan (Irgasan DP300) was obtained from CIBA Specialty Chemicals Corp., High Point, N.C. Brucella Broth (Difco) was rehydrated with double distilled water (28 gl) and heated until a clear solution was obtained. The nutrient was then sterilized in an autoclave for 15 minutes at 15-LB pressure. The final pH of the broth was 7.00 at 25° C. The sterilized nutrient broth was used to culture the bacteria. Freeze dried S. mutans were reconstituted in sterilized polyethylene tubes with 5 ml rehydrated Brucella Broth and incubated at 37° C. for 2 days. After establishment of growth, the bacteria were inoculated onto the agar plates by streaking in four quadrants and allowed to grow at 37° C. After testing for purity and establishment of growth, 100 ul of the reconstituted culture was diluted in 1 ml of sterile water and its optical density was measured at 600 nm. Based on the optical density, appropriate dilutions were made and $10^2$ CFU's were transferred onto the agar plates and spread evenly to establish a "lawn". Then the discs A, AK, B, C, and D (control, kneaded control, 0.25%, 0.5%, 1.0% anti bacterial agent) were placed on the agar surfaces approximately 4 cm apart. The bacteria were then allowed to grow at 37° C. for 48 hours.

The discs were washed 5 times in 5 ml of distilled water to remove all the debris and washing continued for 2 weeks, 2 times daily in 5 ml of distilled water. During this period, the discs were stored in 5 ml distilled water at room temperature. To examine if the antimicrobial agent was still present in these discs, the experiment was repeated as described above.

A separate experiment was conducted using the bacteria P. Aeruginosa, which is the most common source of fingernail and toenail infections.

Figure 1:
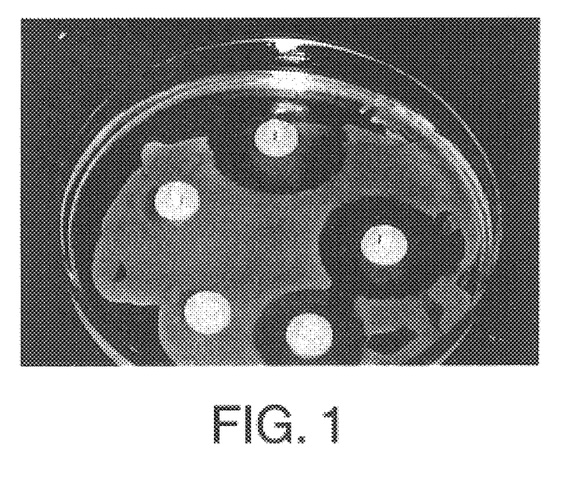
Figure 2:
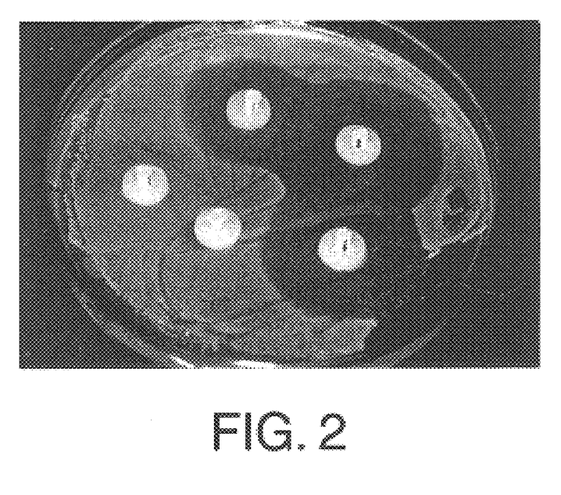

As shown in FIGS. 1 and 2, all of the samples containing triclosan were observed to resist microbial colonization on the surface of and in a well delineated zone around cured disks of the restorative material, whereas the cured control samples without triclosan exhibited marked growth of microorganisms on its surface and in immediate contact with the disks. FIG. 1 depicts a zone of inhibition wherein the growth of S. mutans is inhibited after 48 hours at 37° C. Beginning at the top of FIG. 1 and moving clockwise, the disks are identified as follows: 1.0% triclosan, 0.5% triclosan, 0.25% triclosan, 0.0% triclosan as a control and 0.0% triclosan as a kneaded control. FIG. 2 depicts a zone of inhibition wherein the growth of P. Aeruginosa is inhibited after 48 hours at 37° C. Beginning at the top of FIG. 2 and moving clockwise, the disks are identified as follows: 0.25% triclosan, 1.0% triclosan, 0.5% triclosan, 0.0% triclosan as a control and 0.0% triclosan as a kneaded control.

Specifically, after two days at 37° C., the disc agar diffusion test showed concentration dependent zones of inhibition before and after the two week wash. This indicates that the antimicrobial agent is still active after curing and continues to be released at the levels higher then the MIC of S. mutans after a two week washing period. Control specimens did not show zones of inhibition confirming that the anti microbial activity was due to the anti microbial agent and not the constituents of the composite. The sizes of the "halos" identifying the zones of inhibition are similar before and after the wash suggesting the rate of release is similar, before and after the wash.

The zone of inhibition of the control and kneaded samples was calculated to be 0. In contrast the pre-wash discs containing 0.25% antimicrobial agent showed a mean zone of inhibition of 3.34 mm, the 2 week wash samples showed a zone of inhibition of 3.1 mm. Similarly, the discs containing 0.5% antimicrobial agent showed 3.81 mm and 3.92 mm zones of inhibition for the pre-wash and the post-wash specimens respectively. The discs containing 1.0% antimicrobial agent showed mean zones of inhibition of 5.11 (pre-wash) and 6.1 mm (post-wash). These data are shown in Tables 3 and 4 below.

TABLE 3

Zones of Inhibition (mm)

| Sample | Petri Dish 1 | Petri Dish 2 | Mean |
|---|---|---|---|
| Control | 0 | 0 | 0 |
| Control (Kneaded) | 0 | 0 | 0 |
| 0.0025 | 3.32 | 3.36 | 3.34 |
| 0.005 | 3.83 | 3.8 | 3.81 |
| 0.01 | 5.1 | 5.12 | 5.11 |

TABLE 4

Zones of Inhibition (mm) after 2 week wash

| Sample | Petri Dish 1 | Petri Dish 2 | Mean |
|---|---|---|---|
| Control | 0 | 0 | 0 |
| Control (Kneaded) | 0 | 0 | 0 |
| 0.25% | 3.1 | 3.1 | 3.1 |
| 0.50% | 4.03 | 3.81 | 3.92 |
| 1.00% | 5.6 | 6.6 | 6.1 |

In the present Example, an antimicrobial agent was mixed with ingredients of a composition prior to polymerization. At least a portion of the antimicrobial agent was inert to the polymerization ingredients meaning that at least a portion of the antimicrobial agent did not react with the polymerization ingredients and remain bound within the cure composition. Instead, the antimicrobial agent established a concentration gradient within a zone of inhibition surrounding the cured composition. Other means of incorporating the antimicrobial agent into the composite material, for instance, dissolving the agent in the fluid monomer phase of the composite material prior to the addition of the inorganic filler, are anticipated to provide the same properties as described in the present example.

The results of Example I indicate that the antimicrobial agent is released into the surrounding media in sufficiently high concentrations to inhibit growth of S. mutans and P. Aeruginosa. The zone of inhibition studies showed a concentration dependent zone of inhibition for both the washed and unwashed samples. Furthermore, the zones of inhibition in both the two-week washed and the unwashed samples were similar, suggesting that the antimicrobial agent is released slowly and steadily into the surrounding media at concentrations sufficiently high to inhibit the growth of the organisms tested. Based upon the results shown in Tables 3 and 4, higher concentrations of triclosan, such as up to 4%, should exhibit greater zones of inhibitions than those shown in the tables. Zones of inhibition within the meaning of the present invention include those calculated to be greater than 1 mm, within the range of between about 1 mm to 10 mm, between about 1 mm to about 7 mm, or between about 1 mm to about 6 mm. Zones of inhibition greater than 10 mm or less than 1 mm are also considerd within the scope of embodiments of the present invention.

Accordingly, embodiments of the present invention include the use of the antimicrobial curable compositions in the form of dental restoratives to gradually release one or more antimicrobial agents at the natural tooth/restoration interface to inhibit the growth of S. mutans at the interface and in the cavity preparation. In addition, the antimicrobial agent would be expected to have further benefits by destroying residual S. mutans in the cavity preparation. In addition, embodiments of the present invention include the use of an antimicrobial curable composition in the form of an artificial fingernail or toenail to gradually release one or more antibacterial agents at the natural nail/artificial nail interface to inhibit the growth of P. Aeruginosa at the interface. The antimicrobial compositions of the present invention in the form of dentin and enamel adhesives or "primers" based on adhesion-promoting acrylic monomers, are useful in preventing the interfacial infiltration of microorganisms and the subsequent recurrent caries associated therewith.

According to an alternate embodiment of the present invention, the antimicrobial compositions are used to reduce tooth hypersensitivity as it relates to the presence of S. mutans and the production of acid therefrom. Hence, it is possible that this invention may help in the prevention of tooth hypersensitivity by inhibiting S. mutans in restorations on the root or in the vicinity of the cemento enamel junction. In accordance with that embodiment, a curable composition including an antimicrobial agent is inserted into a desired tooth cavity and allowed to inhibit the growth of S. mutans in a manner to reduce tooth hypersensitivity.

EXAMPLE II
Physical Properties of the Inventive Compositions
Color Stability

The physical properties of the modified composite restorative materials were evaluated, including color stability, compressive strength, and bond strength to dentin. Surprisingly, there was a distinct trend, especially in bond strength to dentin, towards improved physical properties for composite material containing increasing levels of triclosan.

The triclosan and composite restorative material (Kerr, Herculite XRV™) were obtained commercially. The syringes of the composite were emptied and the antimicrobial was incorporated into the composite by kneading as previously described at concentrations of 0.25%, 0.5% and 1% w/w. The composite material was then re-packaged in the original syringes and coded so that the investigators were unaware of the contents of the syringes. Prior to color measurement studies, the syringes were stored at room temperature for two weeks. After this period, 3×15 mm discs were prepared for each sample and the material was light cured for 30 seconds using a commercial curing light. The baseline color of the discs was then measured using a calorimeter with 45-degree/0-degree illumination/observation geometry (Minolta™ CR221) and the color parameters were recorded in the tristimulus L*, a*, b* color space. For each disc six readings were taken at random locations.

The discs were then placed in a Sun Lamp color stability box as specified in the American Dental Association Specification #27 and exposed to UV light for 24 hours. The color was then determined by visual examinations and by the CR221 colorimeter. The calorimeter readings were taken at six random locations. The change in color was evaluated by averaging the tristimulus L*a*b* color parameters and comparing the results of the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978).

$$E = [(L^*)^2 + (a^*)^2 + (b^*)^2]^{1/2}$$

Visual evaluation of the color change according to ADA specifications showed insignificant color changes indicating that the anti microbial can be added to current restorative material formulations without alteration of color. These results were confirmed by colorimeter measurements. As shown in Table 3, the mean color or E (E(Initial))of the control sample (without the anti microbial agent) was calculated to 57.50. The mean E of the kneaded sample was calculated to be 56.64. The mean color value or E for the sample containing 0.25% w/w anti microbial were calculated to be 55.17. The mean color values for samples containing 0.5% and 1.0% antimicrobial were calculated to be 57.26 and 55.31 respectively. Statistical analysis by the F-test (variance of two populations of numbers)] did not show significant differences between the groups hence providing further evidence that addition of the antimicrobial to the restorative material under examination will not cause a significant alteration in color.

After exposure to UV light (E(Final)), the color values for untreated and kneaded controls were calculated to be 57.14 and 56.45 respectively. The E values for 0.25%, 0.5% and 1% were calculated to be 54.42, 57.27, and 55.26 respectively. Statistical analysis by the F test showed a maximum significance level of $p=0.011$ for the controls (kneaded) versus 1% antimicrobial agent strongly suggesting that a larger sample size would yield a significant statistical difference and thus the antimicrobial agent may enhance color stability and prevent UV induced discoloration.

The overall change in color (Change in E) (baseline vs. exposure to light) was calculated using the Commission Internationale de L'Eclairage color difference equation. The change in E for the control, the kneaded samples, the 0.25%, 0.5% and 1.0% triclosan was calculated and is shown in Table 4 below.

TABLE 4

| Sample | E (Initial) | E (Final) | Change in E |
|---|---|---|---|
| Control | 57.5 | 57.14 | −0.36 |
| Kneaded Control | 56.64 | 56.45 | −0.18 |
| +0.25% w/w triclosan | 55.17 | 54.42 | −0.75 |
| +0.50% w/w triclosan | 57.26 | 57.27 | 0.01 |
| +1.00% w/w triclosan | 55.31 | 55.26 | −0.05 |

Collectively, the results shown above indicate that addition of antimicrobial agent to the restorative material tested will not cause an alteration in color. In fact, the results suggest that the antimicrobial agent will cause an improvement in color stability after exposure to UV light.

EXAMPLE III
Compressive Strength/Bond Strength

The following example demonstrates that no significant differences were observed in the compressive strength between control and antimicrobial composite samples.

Triclosan was incorporated into Herculite XRV (Kerr) by emptying the syringes and kneading in the dark at concentrations of 0.25%, 0.5% and 1% w/w. The composite material was then re-packaged in the original syringes and coded so that the investigators were unaware of the contents of the syringes. Freshly extracted human molars were stored in a thymol solution at 3° C. Prior to use, the enamel was removed by using a slow speed diamond saw (Isomet, Beuhler) to obtain flat surfaces and all samples were examined under a light microscope to ensure all the enamel was removed from the test areas. For compressive strength measurements a standard cylindrical stainless steel die was used which allows for curing in 3 mm sections.

To measure compressive strength, the die was filled and compressed up to a level of 3 mm. This was cured with a standard light for 30 seconds. A second 3 mm section was then compressed onto the cured section and again exposed to a curing light for 30 seconds. This was repeated for the third section to obtain 3×9 mm cylindrical specimens. The specimens were then stored at 37° C. in a humidity chamber to obtain complete curing. Compressive strength measurements were carried out using a crosshead-type tensile strength tester (MTS Model 810 Material Testing System) set at a load of 250 N. For each test sample three cylinders were prepared.

Bond strength was measured by compressing the test samples into a gelatin capsule (4 mm diameter and 9 mm length). The capsules were placed onto a glass slide to obtain flat surfaces and cured for 1 minute using a standard dental curing light. After ensuring all the surfaces were flat, the cylinders were bonded onto etched dentin surfaces using Prime & Bond™ (Caulk) system according to the manufacturer's instructions. To each tooth, two samples were bonded and for each sample two teeth were used. Prior to measurements the samples were stored in a humidity chamber for at 37° C. Shear bond strength was measured by using the MTS system under stroke control at a strain rate of 0.02"/min ensuring that knife edge was placed at the dentin-restorative material interface.

The results of the compressive strength are outlined in Table 5 and show no significant differences between the control and antimicrobial composite samples

TABLE 5

| Sample | Compressive Strength (MPa) |
| --- | --- |
| Control | 50.03 (SD = 9.70) |
| Control (Kneaded) | 48.90 (SD = 2.80) |
| 0.25% Triclosan | 48.87 (SD = 2.60) |
| 0.50% Triclosan | 48.24 (SD = 2.88) |
| 1.00% Triclosan | 52.05 (SD = 6.42) |

The results of the bond strength to dentin are shown in Table 6 below.

TABLE 6

| Sample | Shear Bond Strength (MPa) |
| --- | --- |
| Control | 9.74 (SD ± 4.30) |
| Control (Kneaded) | 10.43 (SD ± 3.30) |
| 0.25% Triclosan | 10.53 (SD ± 4.16) |
| 0.50% Triclosan | 13.13 (SD ± 5.94) |
| 1.00% Triclosan | 14.13 (SD ± 6.22) |

Statistical analysis by ANOVA(analysis of variance) did not show any differences between the samples. However, examination of the data showed a directional improvement in the shear bond strength with an increase in concentration of the antimicrobial agent e.g., the dentin-enamel bond strength of control was determined to be 9.74±4.37 MPa while the bond strength of the restorative material containing 1.0% antimicrobial agent was determined to be 14.13±6.22 MPa, which translates into a 45% improvement demonstrating that the antimicrobial composite material of the present invention may provide for an enhancement in the shear bond strength when cured in contact with primed dentin.

The various adhesion promoters in primers and bonding agents used to increase the bond strength of restorative materials to dentin are typically surface-active molecules which are applied to the tooth structure after etching or conditioning. These agents are believed to provide adhesion by bridging the gap between the hydrophilic dentin surface and the hydrophobic composite matrix resin. Although not wishing to be bound by any particular theory, it is speculated that triclosan and other antimicrobial agents with similar molecular properties may in some way alter the interfacial surface tension between the primed dentin surface and the composite restorative material. In addition, the above data suggest that triclosan may increase the color stability of a composite restorative material; the increase in bond strength may be a result of free-radical quenching abilities of triclosan. Free-radical quenchers have been shown to reduce branching of the growing polymer during addition polymerization reactions, an effect which could result in the presence of an interfacial polymer more linear in structure. The reduced branching and high linearity of polymers can result in lower glass transition temperatures and increased tensile strength.

EXAMPLE IV

As the results above suggest that the inclusion of triclosan in a resin-based composite restorative material may increase the overall bond strength to primed dentin, an adhesion-promoting composition was prepared as shown in Table 6 below that would serve as bonding agents between the natural tooth surface (dentin and/or enamel) and a resin-based restorative material. Other priming or bonding agents that would benefit from the inclusion of the water-insoluble antimicrobial compounds described inthe present invention are described in, amount other prior art compositions, U.S. Pat. Nos. 4,514,527; 4,659,751; 5,270,351; 5,276,068, and 4,966,934 each of which are hereby incorporated by reference in their entireties.

TABLE

| Ingredient | Percent (w/w) |
| --- | --- |
| Bis-GMA | 70.00 |
| Triethylene glycol dimethacrylate | 29.55 |
| Camphorquinone | 0.20 |
| Dimethylaminoethyl methacrylate | 0.15 |
| Triclosan | 0.10 |
| TOTAL | 100.00 |

The example shown in Table 6 is an unfilled light-cured resin that is used to bond resin-based composite restorative materials to etched enamel surfaces. The porosity created in the enamel allows for the penetration of the low viscosity resin into the enamel substructure. After curing by exposure to light energy in the range of 400 to 500 nm, the resulting bond is primarily mechanical in nature through the formation of hard resin "tags" that cure within the enamel substructure.

EXAMPLE V

According to another embodiment of the present invention, a solvent-based adhesion promoter containing two different levels of triclosan and useful for bonding the compositions of the present invention to the natural fingernail surface was prepared and tested for adhesion durability, compared to a control adhesion promoter without triclosan. Triclosan was included in the compositions of Table 7 below at the level of 0.3 and 1.0 percent by weight of the non-volatile solids (i.e., exclusive of the ethyl acetate solvent carrier, which rapidly evaporates upon the priming composition's contact with the fingernail surface).

TABLE 7

| Ingredient | Percent (w/w) | | |
| --- | --- | --- | --- |
| | A | B | C |
| Ethyl acetate | 88.24 | 88.2 | 88.13 |
| Methacryloyloxyethyl maleate | 8.75 | 8.75 | 8.75 |
| Hydroxyethyl methacrylate | 2.92 | 2.92 | 2.92 |
| Fluorad FC-430 | 0.08 | 0.08 | 0.08 |
| Triclosan | 0 | 0.03 | 0.12 |
| TOTAL | 100 | 100 | 100 |

Each of the above compositions was evaluated for its adhesion-promoting properties on 40 individuals. None of the evaluators participating in the study were informed of product compositions, and each product in Table 7 was coded in order to blind the study.

A single coat of each priming agent was applied to the natural fingernail surface following a mild abrasion of the nail plate with a nail file. All priming agents were allowed to evaporate until the surface appeared to be dry. In each case, there was a residual gloss on the treated fingernail surface following the evaporation of the ethyl acetate.

Following the application of the priming agent, an artificial fingernail excluding triclosan was "sculpted". Observations as to the artificial fingernails' color, adhesion to the nail plate, and general performance properties were accumulated over a 30 day period.

At the end of the evaluation period, there was a slight preference (although probably not significant) for the priming agent corresponding to Table 7 composition B. Overall, the performance of all of the artificial fingernail priming agents was relatively equal, indicating that the presence of triclosan in the composition does not affect the performance properties of this type of adhesion promoter when present at the artificial fingernail/natural fingernail interface.

EXAMPLE VI

A number of artificial fingernail liquid binder compositions were prepared (similar to those described in U.S. Pat. No. 5,738,843 hereby incorporated by reference in its entirety) that contained varying levels of triclosan. Disks were prepared by combining 1 part of each liquid binder, by weight, with 2 parts of a finely divided polymer consisting of a 70/30 molar ratio poly(ethyl-co-methyl methacrylate) copolymer containing approximately 1.2% by weight of benzoyl peroxide. The benzoyl peroxide in the powder, when combined with the liquid binder (which contains dimethyl-p-toluidine), initiates a free-radical addition polymerization process that renders the liquid binder/powder mixture into a hard, fused mass in approximately 5 minutes.

Very little, if any, difference in the polymerization time was noted between the various mixtures prepared from the liquid binders in Table 8 below, indicating that the inclusion of triclosan did not inhibit the addition polymerization reaction in any significant way. This was somewhat unexpected, due to the sensitivity of most acrylic free-radical polymerization reactions to the presence of aromatic alcohols, such as BHT (butylated hydroxytoluene).

TABLE 8

| Ingredient | Percent (w/w) | | | |
| --- | --- | --- | --- | --- |
| | A | B | C | D |
| Ethyl methacrylate | 83.2 | 82.7 | 82.2 | 81.2 |
| Ethylene glycol dimethacrylate | 6 | 6 | 6 | 6 |
| Isopropyl alcohol | 10 | 10 | 10 | 10 |
| Dimethyl-p-toluidine | 0.8 | 0.8 | 0.8 | 0.8 |
| Triclosan | 0 | 0.5 | 1 | 2 |
| TOTAL | 100 | 100 | 100 | 100 |

EXAMPLE VII

Denture adhesive are typically composed high molecular weight water-soluble polymers dispersed in a hydrophobic carrier, such as petrolatum. When placed in the oral cavity at the interface between a denture and the soft tissue of the mouth, water is absorbed by the dispersed polymer, which gives rise to a sharp increase in the cohesion and viscosity of the composition. By reaching a high viscosity and highly cohesive state can a denture adhesive be described as cured. An example of a useful antimicrobial denture adhesive composition is provided in Table 9 as follows:

TABLE 9

| Ingredient | Percent (w/w) |
| --- | --- |
| Petrolatum | 32.540 |
| Mineral Oil | 14.271 |
| D&C Red #27 Lake | 0.019 |
| Hydrated Silicia | 1.833 |
| Gantrez MS-955 | 32.285 |
| Cellulose Gum | 18.752 |
| Sodium Saccharin | 0.100 |
| Triclosan | 0.200 |
| TOTAL | 100.000 |

The above composition was prepared by dissolving the triclosan in the petrolatum and mineral oil (to which the D&C Red #27 Lake and Sodium saccharin had been added and thoroughly dispersed), which was heated to 150° F. to liquefy the mixture. A dispersion mixer was used to sequentially blend the Hydrated Silicia, the Gantrez MS-955 (IS), Wayne, N.J.), and finally the Cellulose Gum into the above mixture. Mixing was continued until a smooth dispersion was obtained the finished composition was immediately filled into in foil-plastic laminate tubes and sealed.

Similar types of formulations, without the added inventive steps of including a substantially water-insoluble, non-cationic antimicrobial agent, are found throughout the prior art (see, for example, U.S. Pat. No. 5,424,058 incorporated herein by reference in its entirety). In general, such compositions, consist of (1) a water-insoluble carrier, (2) one or more water-swellable polymers in a finely-divided form, dispersed homogeneously throughout the carrier, and (3) various adjuvants, including pigments, dyes, flavorants and preservatives. The water-insoluble carrier portion of the denture adhesive may be hydrophobic organic materials such as petrolatum, mineral oil, waxes, and vegetable oils. Water-swellable polymers finding utility in denture adhesives include poly(ethylene oxide), salts of carboxymethyl cellulose, methyl cellulose, hydroxypropylcellulose, acrylamide polymers, poly (vinylpyrrolidone), and mixed partial salts of poly(methyl vinyl ether-co-maleic and increase inviscosity and cohesion as a result of the absorption of water from the growth medium. Zone of inhibition studies were carried out as previously described in Example I. After 48 hours, the triclosan-containing denture adhesive above exhibited a zone of inhibition of approximately 3–4 mm, while a commercial available denture adhesive did not exhibit a zone of inhibition. In fact, the surface of the commercial denture adhevise was colonized by *S. mutans* after the 48-hour test period. The addition of triclosan to the denture adhesive formulation above resulted in a composition capable of inhibiting microorganisms in the volume surrounding the swollen or cured adhesive mass.

It is to be understood that the embodiments of the present invention which have been described are merely illustrative of some of the applications of the principles of the invention. Numerous modifications may be made by those skilled in the art based upon the teachings presented herein without departing from the true spirit and scope of the invention.

What is claimed is:

1. An artificial fingernail composition, comprising: a polymerizable system and a water-insoluble anti-microbial agent inert to the polymerizable system, wherein said composition is cured to produce an artificial fingernail.

2. An artificial fingernail comprising a cured polymerization system and a water-insoluble anti-microbial agent inert to the polymerization system, wherein said anti-microbial agent provides a zone of inhibition of growth of bacteria surrounding said artificial fingernail.

3. The artificial fingernail of claim 1 wherein said water insoluble antimicrobial agent is selected from the group consisting of halogenated diphenyl ethers, halogenated salicylanilides, benzoic esters, halogenated carbanalides and phenolic compounds.

4. The artificial fingernail of claim 1 wherein said water insoluble antimicrobial agent is triclosan.

5. The artificial fingernail of claim 4 wherein said triclosan is present in an amount of 0.3% by weight of non-volatile solids.

6. The artificial fingernail of claim 4 wherein said triclosan is present in an amount of 1.0% by weight of non-volatile solids.

* * * * *